(12) United States Patent
Lin

(10) Patent No.: US 11,000,620 B2
(45) Date of Patent: May 11, 2021

(54) AROMA DIFFUSER

(71) Applicant: Dongguan Innovation Lighting Co., Ltd., Guangdong (CN)

(72) Inventor: Song Lin, Guangdong (CN)

( * ) Notice: Subject to any disclaimer, the term of this patent is extended or adjusted under 35 U.S.C. 154(b) by 33 days.

(21) Appl. No.: 16/278,175

(22) Filed: Feb. 18, 2019

(65) Prior Publication Data

US 2020/0188548 A1    Jun. 18, 2020

(30) Foreign Application Priority Data

Dec. 18, 2018  (CN) .......................... 201822128357.4

(51) Int. Cl.
*A61L 9/14* (2006.01)
*A61M 21/02* (2006.01)
*A61M 21/00* (2006.01)

(52) U.S. Cl.
CPC .............. *A61L 9/14* (2013.01); *A61M 21/02* (2013.01); *A61L 2209/12* (2013.01); *A61L 2209/134* (2013.01); *A61L 2209/135* (2013.01); *A61M 2021/0016* (2013.01); *A61M 2205/3379* (2013.01); *A61M 2205/587* (2013.01)

(58) Field of Classification Search
CPC ... A61L 9/14; A61L 9/12; A61L 9/125; A61L 9/122; A61L 9/141; A61L 9/145; A61L 2209/12; A61L 2209/134; A61L 2209/135; A61L 2021/0016; A61L 2205/3379; A61L 2205/587; A01M 21/02
See application file for complete search history.

(56) References Cited

U.S. PATENT DOCUMENTS

| 2006/0072325 A1* | 4/2006 | Lewis | B60Q 1/326 362/276 |
| 2014/0263723 A1* | 9/2014 | Hsiao | B05B 17/0615 239/102.2 |
| 2019/0096293 A1* | 3/2019 | Kwon | F21V 9/40 |

* cited by examiner

*Primary Examiner* — Tuongminh N Pham
(74) *Attorney, Agent, or Firm* — Prakash Nama; Global IP Services, PLLC

(57) ABSTRACT

An aroma diffuser having a base, and an essential oil container cylinder above the base and sleeved by an outer shell; a circuit board and an atomizing transducer are provided inside the base; an energy accumulation aperture is provided at a bottom plate of the essential oil container cylinder; the atomizing transducer is mounted at a lower end of the energy accumulation aperture; a width of the atomizing transducer is greater than a width of the energy accumulation aperture; a light column is provided inside the essential oil container cylinder; a light source is mounted inside the light column; an upper cover is provided at an upper end of the essential oil container cylinder; a light blocking shade is provided at an upper end of the upper cover; a first opening is provided on the upper cover; a gas discharge opening is provided on the light blocking shade.

7 Claims, 4 Drawing Sheets

AROMA DIFFUSER

BACKGROUND OF THE INVENTION

The present disclosure relates to the technical field of aroma diffuser, and more specifically relates to an improved aroma diffuser.

A major function of an aroma diffuser is to atomize or vaporize added liquid substances to aromatize the air, improve air quality and increase air humidity etc. For example, by using different kinds of liquid, in other words, essential oil, beneficial and therapeutic effects for beauty, health and general well-being can be achieved, for example improving memory, reducing insomnia, soothing emotions, and alleviating anxiety-induced headaches etc. Following the continuous technological developments, demands and requirements for aroma diffuser are getting higher. A conventional aroma diffuser can no longer satisfy the pursuit of fashion in the market. A 5V atomizer now available in the market has a very ineffective atomizing transducer due to the constraints of voltage and power of USB. Therefore, an energy accumulation ring has to be placed at an upper end of an atomizer energy accumulation aperture to create a certain amount of vapor, thereby complicating the overall structure of the atomizer and increasing the cost of production. Also, such atomizer is not easy to be cleaned. Moreover, the atomizing transducer currently available in the market has a width equivalent to the position in the water tank mounting the same, therefore resulting in very low water pressure and power, and generating only a small amount of vapor.

BRIEF SUMMARY OF THE INVENTION

In view of the disadvantages of the prior art described above, the present invention provides an improved aroma diffuser which is structurally simple and easy to use. By providing a light column and a light source, a ring of light can be emitted from the aroma diffuser, thereby presenting a novel and fashionable design.

To achieve the above objects of the present invention, the present invention has the following technical solutions:

An improved aroma diffuser, comprising a body; the body comprises a base and an essential oil container cylinder which is made of transparent or semi-transparent material; the essential oil container cylinder is positioned above the base; the essential oil container cylinder is sleeved by an outer shell which has a cylindrical shape; a circuit board and an atomizing transducer connected to the circuit board are provided inside the base; an energy accumulation aperture is provided at a bottom plate of the essential oil container cylinder; the atomizing transducer is mounted at a lower end the energy accumulation aperture; a width of the atomizing transducer is greater than a width of the energy accumulation aperture; a silica water proof ring is provided around a periphery of the atomizing transducer; a light column is provided inside the essential oil container cylinder; a light source is mounted inside the light column; a removable upper cover is provided at an upper end of the essential oil container cylinder; a light blocking shade is provided at an upper end of the upper cover; peripheries of the light blocking shade are positioned proximal to an inner side of a periphery of the outer shell; a first opening is provided on the upper cover to allow vapor to exit from the essential oil container cylinder; a gas discharge opening corresponding to the first opening and having an enlarging diameter away from the first opening is provided on the light blocking shade; the gas discharge opening is in communication with the first opening.

Preferably, an inner side wall of the outer shell is spaced apart from an outer side wall of the essential oil container cylinder.

Preferably, an outer side of the essential oil container cylinder is provided with a platform extending outwardly; the platform has a width corresponding to a thickness of the outer shell.

Preferably, the light source is an LED light bead.

Preferably, a USB port and a control switch are also provided on the base.

Preferably, a mounting seat is provided on the base; the atomizing transducer is mounted at the lower end of the energy accumulation aperture via the mounting seat.

Preferably, a water level detection device is provided inside the essential oil container cylinder.

Preferably, the atomizing transducer has a circular planar shape, or has a circular shape having a depression in a middle part thereof.

The present invention has the following beneficial effects: The essential oil container cylinder is provided with the light column inside; the light column has the light source inside; the upper end of the essential oil container cylinder has the removable upper cover; the upper end of the upper cover is provided with the light blocking shade; the peripheries of the light blocking shade are positioned proximal to the inner side of the periphery of the outer shell; the lights from the light source emit out of the upper cover, and by the light blocking effect of the light blocking shade, the lights form a shape of a ring between the light blocking shade and the upper cover, thereby achieving a novel and fashionable design. The width of the atomizing transducer is greater than the width of the energy accumulation aperture, and due to the increased width of the atomizing transducer compared with the prior art, the energy accumulation aperture can be reduced in size, thereby causing more energy to be accumulated in the energy accumulation aperture so as to increase the amount of vapor generated; accordingly, an energy accumulation ring is no longer required, thereby simplifying the structure and reducing power consumption.

In order to illustrate more clearly the structural features, technical solutions and the objects and functions achieved by the present invention, the present invention will be further described in detail below with reference to the drawings and embodiments.

References in the figures: 10—body; 11—base; 12—essential oil container cylinder; 121—energy accumulation aperture; 122—light column; 123—platform; 124—LED light bead; 13—outer shell; 14—atomizing transducer; 15—upper cover; 151—first opening; 16—light blocking shade; 17—gas discharge opening; 18—USB port.

DETAILED DESCRIPTION OF THE INVENTION

Figure 1:
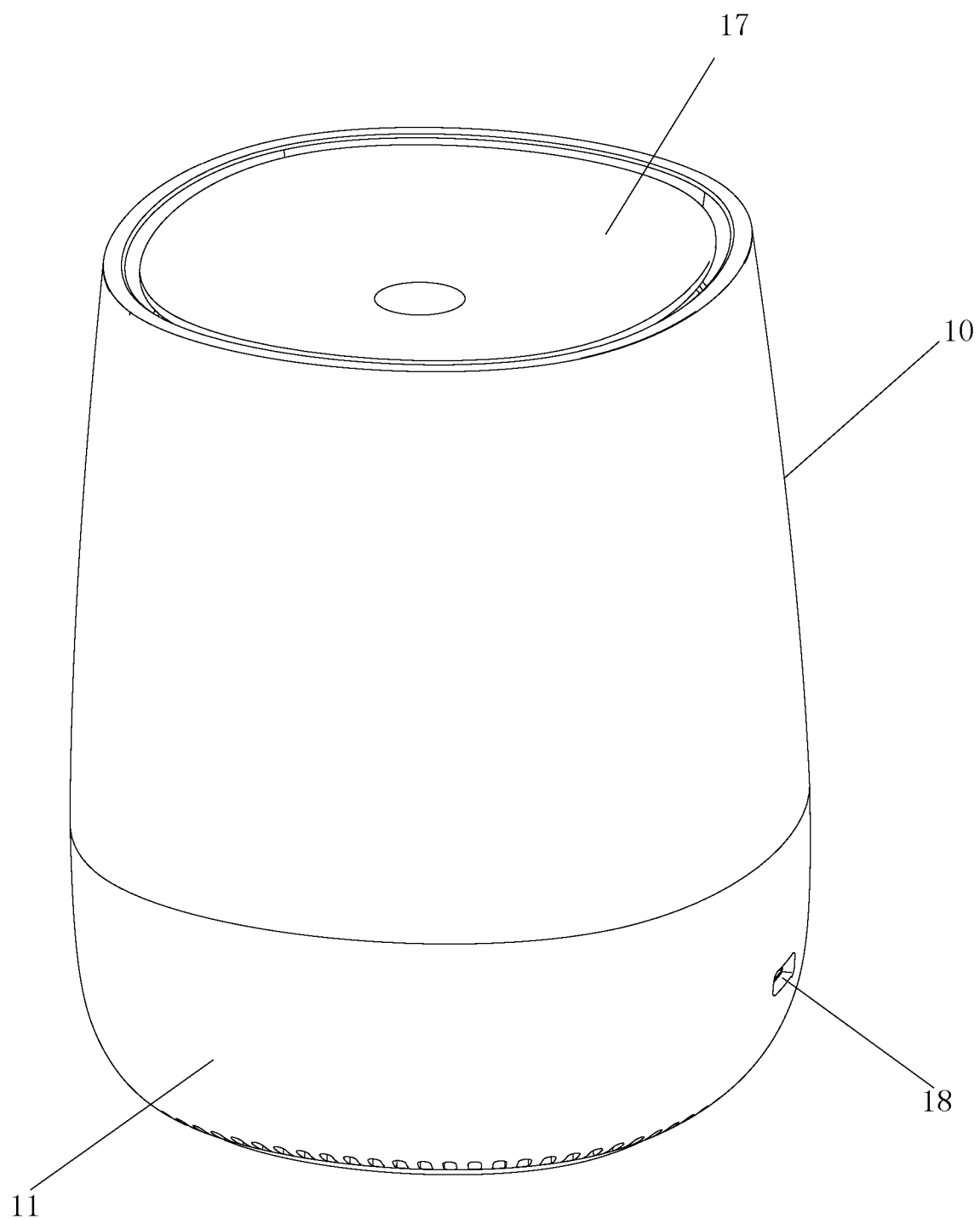
FIG. 1 is an assembled structural view of the present invention according to an embodiment.
Figure 2:
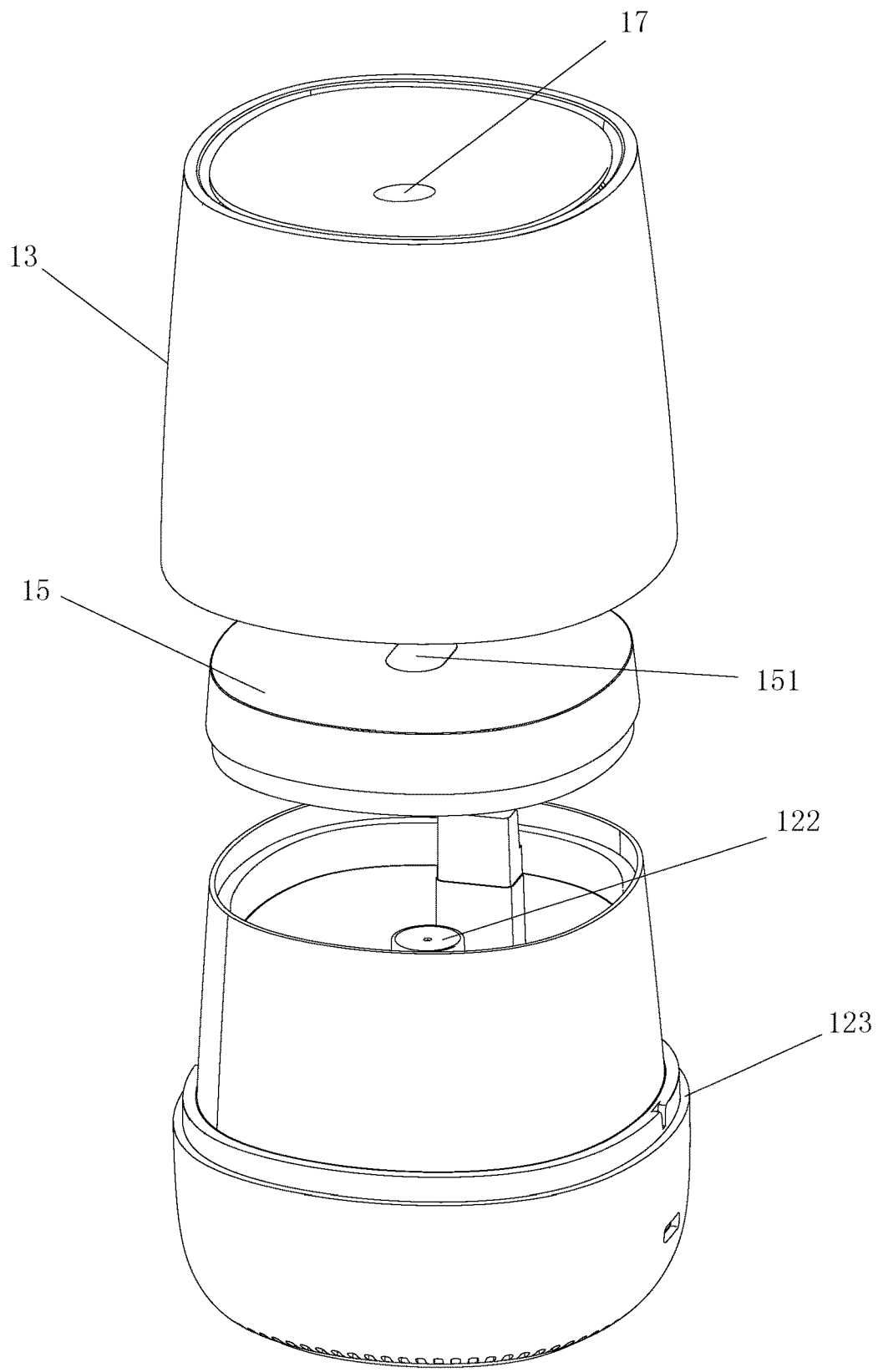
FIG. 2 is an exploded structural view of the present invention according to an embodiment.
Figure 3:
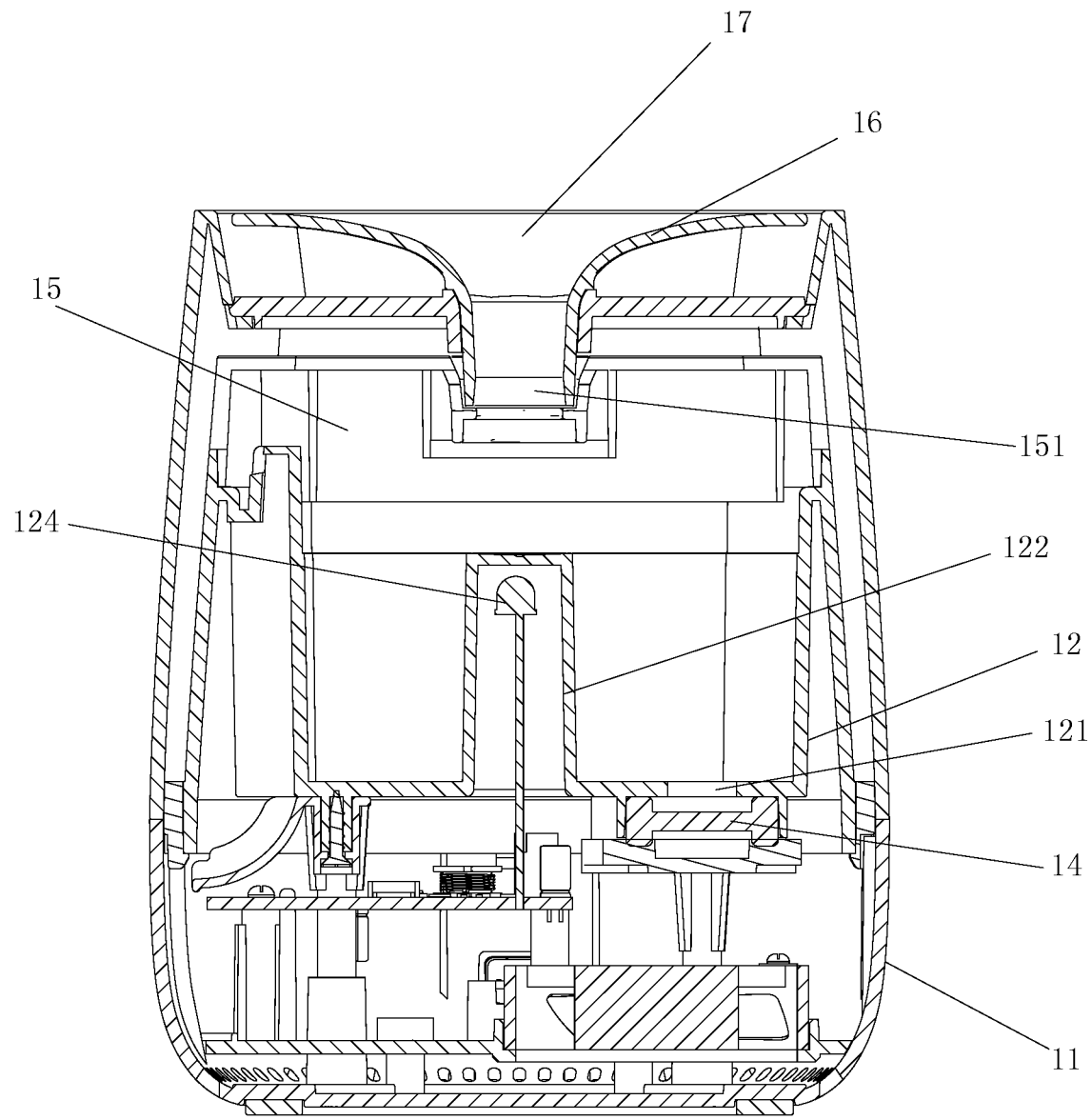
FIG. 3 is a sectional view of the present invention according to an embodiment.

As shown in FIGS. 1-3, an improved aroma diffuser comprises a body 10; the body 10 comprises a base 11 and an essential oil container cylinder 12 which is made of transparent or semi-transparent material; the essential oil container cylinder 12 is positioned above the base 11; the essential oil container cylinder 12 is sleeved by an outer shell 13 which has a cylindrical shape; an inner side wall of the outer shell 13 is spaced apart from an outer side wall of the essential oil container cylinder 12; an outer side of the essential oil container cylinder 12 is provided with a platform 123 extending outwardly; the platform 123 has a width corresponding to a thickness of the outer shell 13; a circuit board and an atomizing transducer 14 connected to the circuit board are provided inside the base 11; an energy accumulation aperture 121 is provided at a bottom plate of the essential oil container cylinder 12; the atomizing transducer 14 is mounted below the energy accumulation aperture 121 via a mounting seat; a width of the atomizing transducer 14 is greater than a width of the energy accumulation aperture 121; a silica water proof ring is provided around a periphery of the atomizing transducer 14; by increasing the width of the atomizing transducer compared to the prior art, the energy accumulation aperture 121 can be reduced in size, so that 5V energy will not disperse, thereby increasing an amount of vapor produced without adding an energy accumulation ring at an upper end of the energy accumulation aperture 121. A light column 122 and a water level detection device are provided inside the essential oil container cylinder 12; a light source is mounted inside the light column 122; the light source can be an LED light bead 124. A removable upper cover 15 is provided at an upper end of the essential oil container cylinder 12; a light blocking shade 16 is provided at an upper end of the upper cover 15; peripheries of the light blocking shade 16 are positioned proximal to an inner side of a periphery of the outer shell 13; lights are emitted from the light source out of the upper cover 15, and due to the light blocking effect of the light blocking shade 16, the lights form a shape of a ring between the light blocking shade 16 and the outer shell 13, thereby achieving a novel and fashionable design. A first opening 151 is provided on the upper cover 15 to allow vapor to exit; a gas discharge opening 17 corresponding to the first opening 151 and having an enlarging diameter away from the first opening 151 is provided on the light blocking shade 16; the gas discharge opening 17 is in communication with the first opening 151. A USB port 18 and a control switch are also provided on the base 11. In this embodiment, the atomizing transducer 14 has a circular planar shape.

Figure 4:
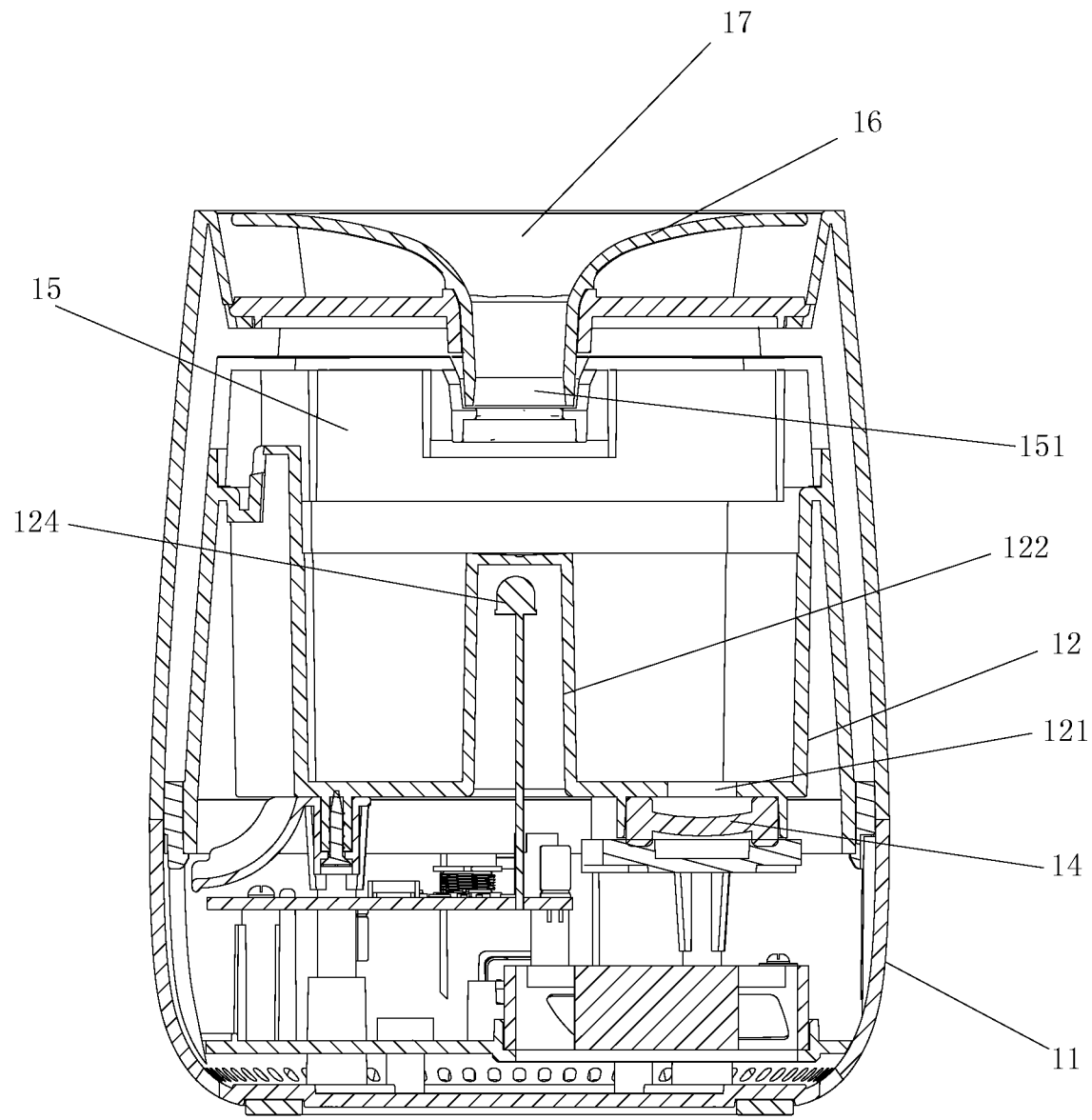
FIG. 4 is a sectional view of the present invention according to another embodiment.

FIG. 4 shows a second embodiment of the present invention. The second embodiment is different from the first embodiment in that, the atomizing transducer 14 has a curved shape depression in a middle part thereof.

Only the more preferred embodiments of the present invention are described above. The embodiments as described are not intended to limit the present invention. Any changes, modifications, or replacements achieving the same technical effects made according to the essence of the teachings of the present invention should also fall within the scope of protection of the present invention.

What is claimed is:

1. An aroma diffuser, comprising a body; the body comprises a base and an essential oil container cylinder which is made of transparent or semi-transparent material; the essential oil container cylinder is positioned above the base; the essential oil container cylinder is sleeved by an outer shell which has a cylindrical shape; a circuit board and an atomizing transducer connected to the circuit board are provided inside the base; an energy accumulation aperture is provided at a bottom plate of the essential oil container cylinder; the atomizing transducer is mounted at a lower end of the energy accumulation aperture; a width of the atomizing transducer is greater than a width of the energy accumulation aperture; a silica water proof ring is provided around a periphery of the atomizing transducer; a light column is provided inside the essential oil container cylinder; a light source is mounted inside the light column; a removable upper cover is provided at an upper end of the essential oil container cylinder; a light blocking shade is provided at an upper end of the upper cover; an upper periphery of the light blocking shade is positioned adjacent to an inner side of a periphery of the outer shell; a first opening is provided on the upper cover to allow vapor to exit from the essential oil container cylinder; a gas discharge opening corresponding to the first opening and having an enlarging diameter away from the first opening is provided on the light blocking shade; the gas discharge opening is in communication with the first opening.

2. The aroma diffuser of claim 1, wherein an inner side wall of the outer shell is spaced apart from an outer side wall of the essential oil container cylinder.

3. The aroma diffuser of claim 2, wherein an outer side of the essential oil container cylinder is provided with a platform extending outwardly; the platform has a width corresponding to a thickness of the outer shell.

4. The aroma diffuser of claim 1, wherein the light source is an LED light bead.

5. The aroma diffuser of claim 1, wherein a USB port and a control switch are also provided on the base.

6. The aroma diffuser of claim 1, wherein a mounting seat is provided on the base; the atomizing transducer is mounted at the lower end of the energy accumulation aperture via the mounting seat.

7. The aroma diffuser of claim 1, wherein the atomizing transducer has a circular planar shape, or has a circular shape having a depression in a middle part of the circular shape.

* * * * *